United States Patent
Dinino et al.

(10) Patent No.: US 11,129,609 B2
(45) Date of Patent: Sep. 28, 2021

(54) DEVICES, SYSTEMS, AND METHODS FOR PROVIDING SURGICAL ACCESS AND FACILITATING CLOSURE OF SURGICAL ACCESS OPENINGS

(71) Applicant: Covidien LP, Mansfield, MA (US)

(72) Inventors: Matthew A. Dinino, Newington, CT (US); Jacob C. Baril, Norwalk, CT (US); Kevin Desjardin, Cheshire, CT (US); Eric Brown, Haddam, CT (US)

(73) Assignee: Covidien LP, Mansfield, MA (US)

( * ) Notice: Subject to any disclaimer, the term of this patent is extended or adjusted under 35 U.S.C. 154(b) by 329 days.

(21) Appl. No.: 16/261,838

(22) Filed: Jan. 30, 2019

(65) Prior Publication Data

US 2019/0321028 A1 Oct. 24, 2019

Related U.S. Application Data

(60) Provisional application No. 62/661,861, filed on Apr. 24, 2018.

(51) Int. Cl.
*A61B 17/04* (2006.01)
*A61B 17/34* (2006.01)
*A61B 17/00* (2006.01)

(52) U.S. Cl.
CPC ...... *A61B 17/0469* (2013.01); *A61B 17/0485* (2013.01); *A61B 17/3423* (2013.01); *A61B 2017/00367* (2013.01); *A61B 2017/047* (2013.01)

(58) Field of Classification Search
CPC .......... A61B 17/0469; A61B 17/0485; A61B 2017/00367; A61B 2017/047; A61B 17/0483; A61B 17/06066; A61B 17/0487
See application file for complete search history.

(56) References Cited

U.S. PATENT DOCUMENTS

| | | | |
|---|---|---|---|
| 987,173 | A | 3/1911 | Sale |
| 2,212,013 | A | 8/1940 | Devareaux |
| 4,655,219 | A | 4/1987 | Petruzzi |
| 5,364,410 | A | 11/1994 | Failla et al. |
| 5,431,666 | A | 7/1995 | Sauer et al. |
| 5,496,335 | A * | 3/1996 | Thomason ......... A61B 17/0469 606/148 |

(Continued)

FOREIGN PATENT DOCUMENTS

| | | |
|---|---|---|
| EP | 2412317 A1 | 2/2012 |
| WO | 9502998 A1 | 2/1995 |

(Continued)

OTHER PUBLICATIONS

International Search Report from corresponding PCT/US2014/048892 dated Nov. 25, 2014.

(Continued)

*Primary Examiner* — Katrina M Stransky

(57) ABSTRACT

A suture passer includes a handle assembly, a shaft extending distally from the handle assembly, an end effector assembly coupled to a distal end portion of the shaft, and an overstroke assembly. The overstroke assembly effects an opening and a closing of the end effector assembly while also preventing an overstroke of the handle assembly from damaging components of the suture passer.

24 Claims, 9 Drawing Sheets

(56) References Cited

U.S. PATENT DOCUMENTS

| | | | |
|---|---|---|---|
| 5,499,997 A | 3/1996 | Sharpe et al. | |
| 5,507,755 A | 4/1996 | Gresl et al. | |
| 5,522,846 A | 6/1996 | Bonutti | |
| 5,540,704 A | 7/1996 | Gordon et al. | |
| 5,562,688 A | 10/1996 | Riza | |
| 5,613,974 A | 3/1997 | Andreas et al. | |
| 5,653,716 A | 8/1997 | Malo et al. | |
| 5,674,230 A * | 10/1997 | Tovey | A61B 17/0469 606/139 |
| 5,700,273 A | 12/1997 | Buelna et al. | |
| 5,716,369 A | 2/1998 | Riza | |
| 5,741,278 A | 4/1998 | Stevens | |
| 5,772,672 A | 6/1998 | Toy et al. | |
| 5,814,065 A | 9/1998 | Diaz | |
| 5,817,108 A | 10/1998 | Poncet | |
| 5,817,111 A | 10/1998 | Riza | |
| 5,836,955 A | 11/1998 | Buelna et al. | |
| 5,860,990 A | 1/1999 | Nobles et al. | |
| 5,899,911 A * | 5/1999 | Carter | A61B 17/06066 606/148 |
| 5,938,668 A | 8/1999 | Scirica et al. | |
| 5,954,734 A | 9/1999 | Thomason et al. | |
| 5,993,474 A | 11/1999 | Ouchi | |
| 6,022,360 A | 2/2000 | Reimels et al. | |
| 6,042,601 A * | 3/2000 | Smith | A61B 17/0057 606/139 |
| 6,099,550 A | 8/2000 | Yoon | |
| 6,110,185 A | 8/2000 | Barra et al. | |
| 6,117,144 A | 9/2000 | Nobles et al. | |
| 6,183,485 B1 | 2/2001 | Thomason et al. | |
| 6,270,508 B1 * | 8/2001 | Klieman | A61B 17/062 606/147 |
| 6,641,592 B1 | 11/2003 | Sauer et al. | |
| 6,743,242 B2 | 6/2004 | Guo | |
| 7,842,049 B2 | 11/2010 | Voss | |
| 7,875,043 B1 | 1/2011 | Ashby et al. | |
| 8,109,943 B2 | 2/2012 | Boraiah et al. | |
| 8,172,801 B2 | 5/2012 | Adams | |
| 9,700,303 B2 | 7/2017 | Prior et al. | |
| 2003/0220658 A1 * | 11/2003 | Hatch | A61B 17/06066 606/139 |
| 2004/0068273 A1 | 4/2004 | Fariss et al. | |
| 2004/0087978 A1 | 5/2004 | Velez et al. | |
| 2005/0212221 A1 | 9/2005 | Smith et al. | |
| 2005/0228405 A1 | 10/2005 | Maruyama et al. | |
| 2006/0135991 A1 | 6/2006 | Kawaura et al. | |
| 2006/0142784 A1 | 6/2006 | Kontos | |
| 2007/0250112 A1 | 10/2007 | Ravikumar et al. | |
| 2007/0270885 A1 * | 11/2007 | Weinert | A61B 17/0625 606/139 |
| 2010/0012152 A1 | 1/2010 | Hansen | |
| 2010/0016870 A1 | 1/2010 | Campbell | |
| 2010/0179572 A1 | 7/2010 | Voss et al. | |
| 2010/0262166 A1 | 10/2010 | Boraiah et al. | |
| 2011/0082475 A1 | 4/2011 | Smith | |
| 2011/0112557 A1 | 5/2011 | Beeley | |
| 2011/0237901 A1 | 9/2011 | Duke et al. | |
| 2011/0245850 A1 | 10/2011 | van der Burg et al. | |
| 2011/0288563 A1 | 11/2011 | Gianotti et al. | |
| 2012/0029532 A1 | 2/2012 | Hodgkinson et al. | |
| 2012/0035623 A1 | 2/2012 | Bagaoisan et al. | |
| 2012/0116422 A1 * | 5/2012 | Triplett | A61B 17/0469 606/144 |
| 2012/0123448 A1 | 5/2012 | Flom et al. | |
| 2012/0143221 A1 | 6/2012 | Weisel et al. | |
| 2013/0006277 A1 | 1/2013 | Stafford | |
| 2013/0079597 A1 | 3/2013 | Auerbach et al. | |
| 2013/0165956 A1 | 6/2013 | Sheds et al. | |
| 2015/0157317 A1 | 6/2015 | Bagaoisan et al. | |

FOREIGN PATENT DOCUMENTS

| | | |
|---|---|---|
| WO | 2011128392 A1 | 10/2011 |
| WO | 2012093094 A1 | 7/2012 |
| WO | 2013105993 A2 | 7/2013 |
| WO | 2017059587 A1 | 4/2017 |
| WO | 2017075752 A1 | 5/2017 |

OTHER PUBLICATIONS

International Search Report from corresponding PCT/US2014/048919 dated Nov. 7, 2014.

International Search Report from corresponding PCT/US2014/048907 dated Nov. 12, 2014.

Extended European Search Report corresponding to counterpart Int'l Appln. No. EP 14 83 1785.2, dated Mar. 17, 2017.

Extended European Search Report corresponding to counterpart Int'l Appln. No. EP 14 83 2198.7 dated Apr. 18, 2017.

European Search Report dated Sep. 20, 2019, corresponding to counterpart European Application No. 19170620.9; 7 pages.

* cited by examiner

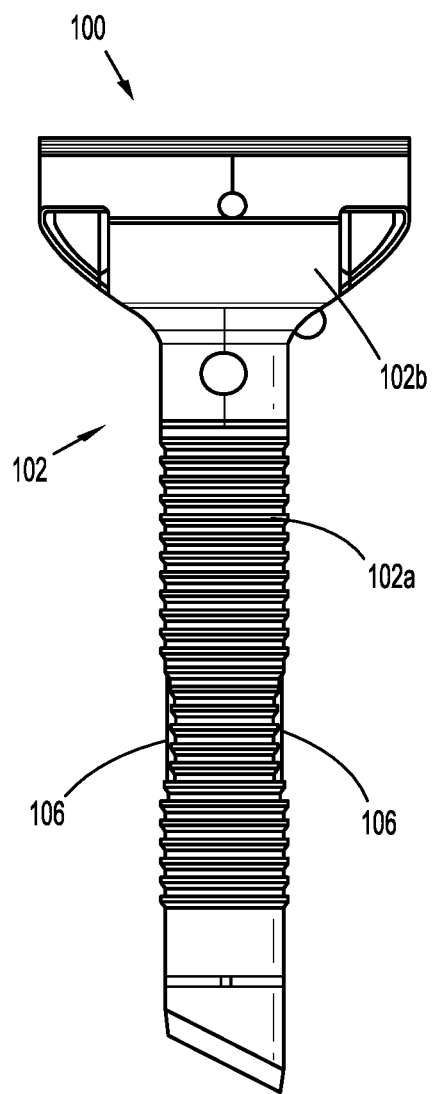
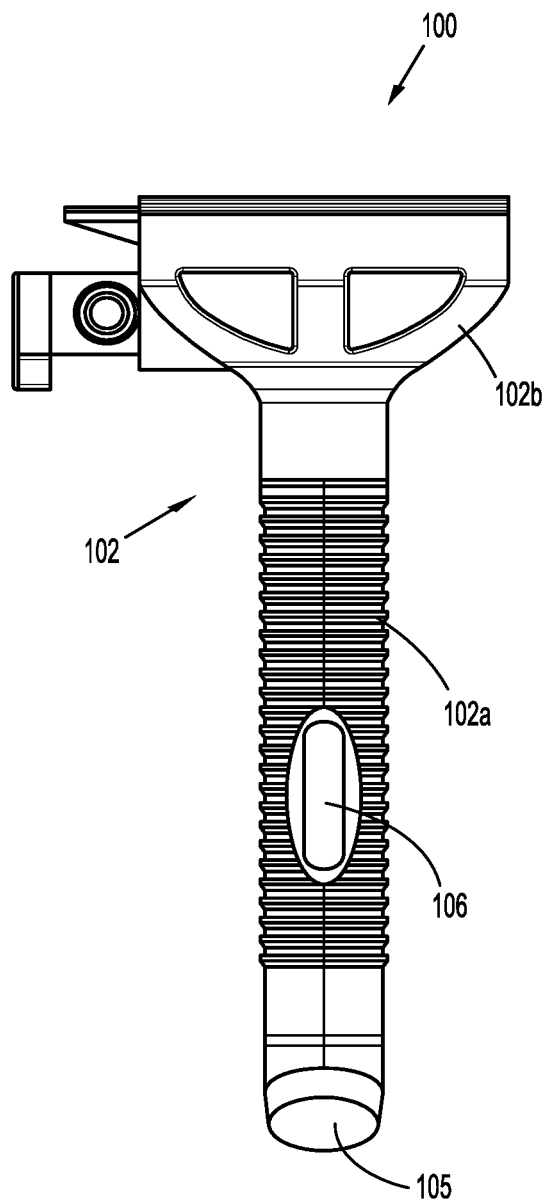
FIG. 3A  FIG. 3B

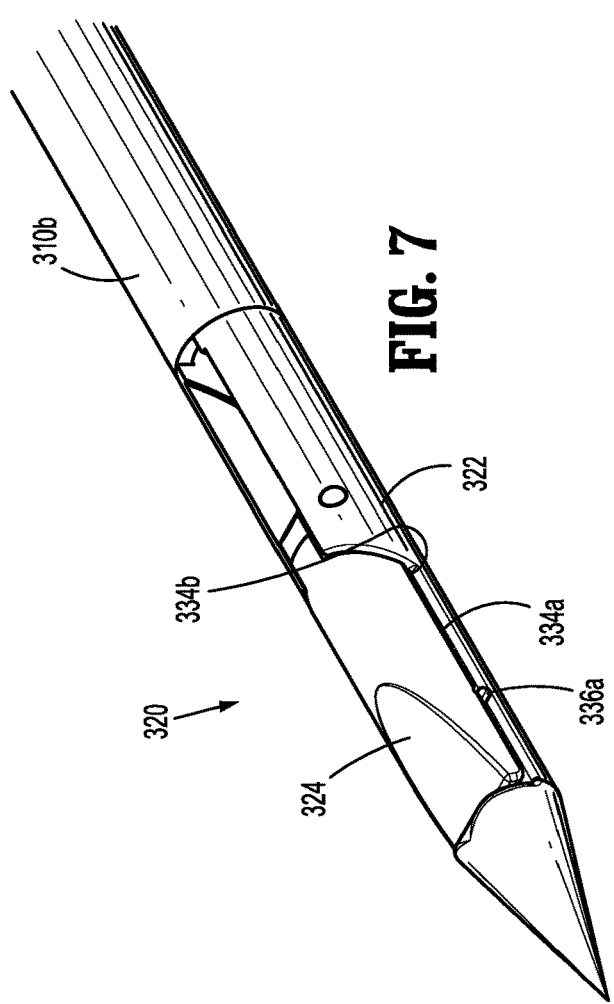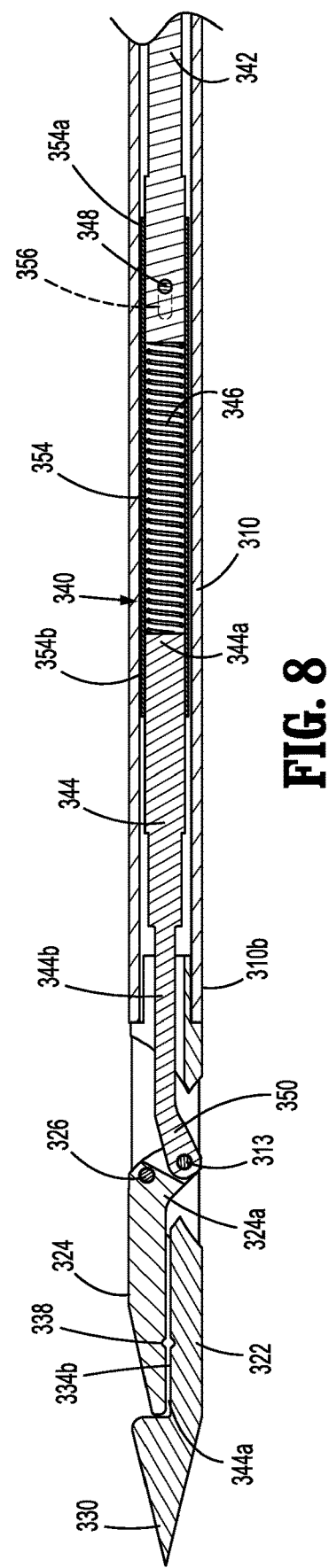

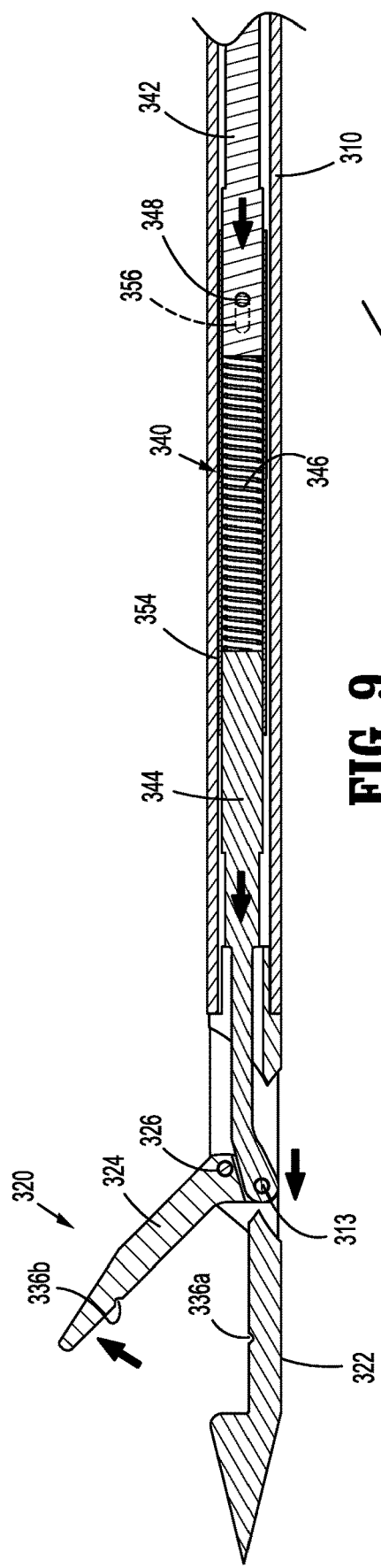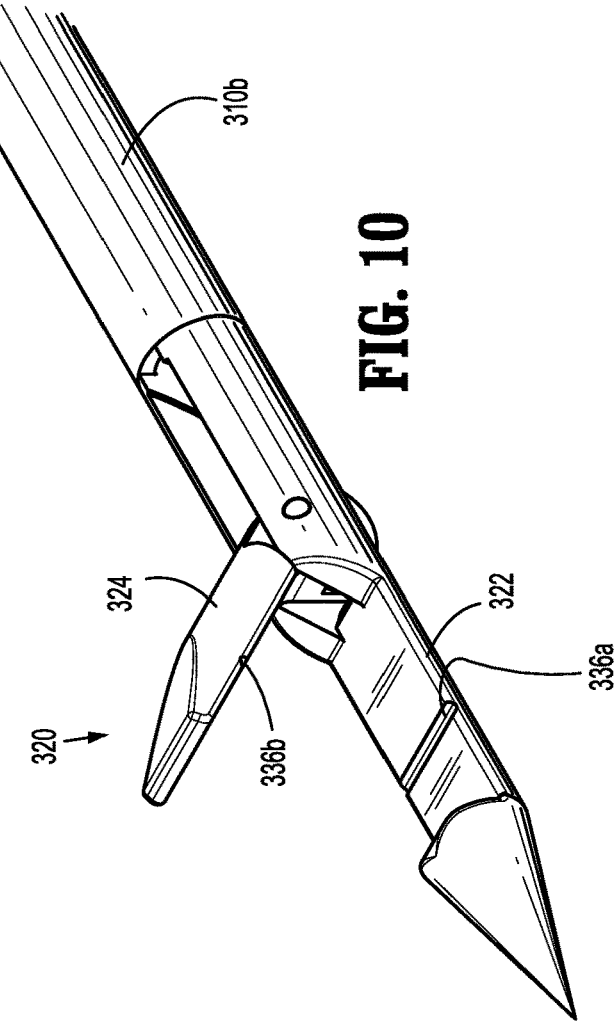

DEVICES, SYSTEMS, AND METHODS FOR PROVIDING SURGICAL ACCESS AND FACILITATING CLOSURE OF SURGICAL ACCESS OPENINGS

CROSS-REFERENCE TO RELATED APPLICATION

This application claims the benefit of and priority to U.S. Provisional Patent Application No. 62/661,861 filed Apr. 24, 2018, the entire disclosure of which is incorporated by reference herein.

BACKGROUND

Technical Field

The present disclosure relates to surgical access and closure of surgical access openings and, more particularly, to devices, systems, and methods that provide access to an internal surgical site through an opening in tissue and facilitate the closure of the opening in tissue.

Background of Related Art

Puncture wounds (i.e., wounds that pierce through tissue) may result from trauma or may be intentionally created in order to provide a surgical access opening for accessing an internal surgical site of a patient during surgical procedures. During endoscopic surgical procedures, for example, a trocar device is utilized to puncture the peritoneum to provide access by way of a cannula through the abdominal wall. Generally, a trocar and/or cannula is placed through the abdominal wall for introduction of surgical instrumentation which is necessary to carry out one or more surgical tasks. The surgeon may introduce a surgical instrument such as a forceps, scissors, clip applier, stapler, biopsy device, or any other suitable surgical instrument as necessary to complete a particular surgical task or tasks. Once the task(s) is complete, it is necessary to close the opening.

A continuing need exists in the surgical arts for improved tools and methods for safely closing puncture openings in a body wall of a patient.

SUMMARY

The present disclosure provides devices, systems, and methods that facilitate accessing an internal surgical site through an opening in tissue, performing one or more minimally-invasive surgical tasks within the internal surgical site, and closing the opening in tissue once the surgical task(s) is complete. In particular, in accordance with aspects of the present disclosure, a suture passer is provided. The suture passer includes a handle assembly, a shaft extending distally from the handle assembly, a first jaw member coupled to a distal end portion of the shaft, a second jaw member pivotable relative to the first jaw member between open and closed configurations, and an overstroke assembly. The overstroke assembly includes a proximal actuator rod operably coupled to the handle assembly, a distal actuator rod axially movable relative to the shaft and operably coupled to the second jaw member, and a biasing member interposed between the proximal and distal actuator rods. Advancement of the proximal actuator rod in response to an actuation of the handle assembly advances the biasing member and the distal actuator rod. The biasing member is configured to compress to allow for independent movement of the proximal actuator rod relative to the distal actuator rod in response to an obstruction of the second jaw member.

In aspects, the overstroke assembly may further include a sleeve disposed within the shaft and longitudinally movable relative to the shaft. The sleeve may be disposed about the proximal and distal actuator rods and may house the biasing member.

In aspects, the sleeve may define a longitudinally-extending slot, and the proximal actuator rod may have a pin slidably received in the slot.

In aspects, when the second jaw member is prevented from opening by an obstruction, an actuation of the handle assembly may distally move the pin from a proximal position within the slot to a distal position within the slot.

In aspects, the proximal actuator rod may be configured to move relative to the sleeve and the distal actuator rod during the distal movement of the pin toward the distal position.

In aspects, the pin may be configured to proximally move the sleeve and the distal actuator rod to move the second jaw member toward the closed configuration in response to an actuation of the handle assembly.

In aspects, the distal actuator rod may be fixed within the sleeve, and the proximal actuator rod may be slip-fit within the sleeve.

In aspects, the second jaw member may have a proximal end portion pivotably coupled to the distal actuator rod.

In aspects, the first jaw member may have a distal tip configured to pierce tissue.

In aspects, the second jaw member may be nested with the first jaw member in the closed configuration.

In aspects, the first jaw member may define a recessed portion configured to receive the second jaw member when the second jaw member is in the closed configuration.

In aspects, each of the first and second jaw members may have a suture-contacting surface defining a transverse notch therein. The transverse notches of the first and second jaw members may be configured to cooperatively enclose a suture therein.

In another aspect of the present disclosure, a suture passer includes a handle assembly, a shaft extending distally from the handle assembly, and an end effector assembly. The end effector assembly includes a first jaw member coupled to a distal end portion of the shaft and a second jaw member pivotable relative to the first jaw member between open and closed configurations. The suture passer further includes a proximal actuator rod, a distal actuator rod, and a biasing member interposed between the proximal and distal actuator rods. The proximal actuator rod is operably coupled to a trigger of the handle assembly, such that a first actuation of the trigger proximally moves the proximal actuator rod. The distal actuator rod is slidably disposed within the shaft and operably coupled to the second jaw member. The proximal actuator rod is configured to distally move the distal actuator rod via the biasing member in response to a second actuation of the handle assembly. The biasing member is configured to compress between the proximal and distal actuator rods upon the proximal actuator rod exerting a distally-oriented, threshold force on the biasing member.

In aspects, the distal actuator rod may be pivotably coupled to the second jaw member via a pivot pin configured to receive a distally-oriented force from the distal actuator rod. The distally-oriented, threshold force imparted on the biasing member may be lower than a threshold force required to damage the pivot pin.

In aspects, when the second jaw member is prevented from opening by an obstruction, the second actuation of the trigger may distally move the proximal actuator rod relative to the distal actuator rod to compress the biasing member therebetween.

In aspects, the suture passer may further include a sleeve disposed within the shaft and longitudinally movable relative to the shaft. The sleeve may be disposed about the proximal and distal actuator rods and may house the biasing member.

In aspects, the sleeve may define a longitudinally-extending slot, and the proximal actuator rod may have a pin slidably received in the slot.

In aspects, when the second jaw member is prevented from opening by an obstruction, the second actuation of the trigger may distally move the pin from a proximal position within the slot to a distal position within the slot.

In aspects, the proximal actuator rod may be configured to move relative to the sleeve and the distal actuator rod during the distal movement of the pin toward the distal position.

In aspects, the pin may be configured to proximally move the sleeve and the distal actuator rod to move the second jaw member toward the closed configuration in response to the first actuation of the trigger.

In aspects, the distal actuator rod may be fixed within the sleeve, and the proximal actuator rod may be slip-fit within the sleeve.

In yet another aspect of the present disclosure, a method of depositing a portion of a suture into an internal surgical site and/or retrieving a portion of suture from within an internal surgical site is provided. The method includes advancing a suture passer into a surgical site while first and second jaw members of the suture passer are in a closed configuration; and actuating a handle assembly of the suture passer. Actuating the handle assembly one of: distally moves a proximal actuator rod toward a distal actuator rod; or distally moves the proximal actuator rod, the biasing member, and the distal actuator rod together. Distal movement of the proximal actuator rod toward the distal actuator rod compresses a biasing member between the proximal actuator rod and the distal actuator. The proximal actuator rod is operably coupled to the handle assembly and the distal actuator rod is operably coupled to the second jaw member. Distal movement of the proximal actuator rod, the biasing member, and the distal actuator rod together pivots the second jaw member relative to the first jaw member to transition the first and second jaw members to the open configuration for one of depositing a portion of suture into the internal surgical site or retrieving a portion of the suture from the internal surgical site.

In some methods, the biasing member may be compressed between the proximal and distal actuator rods when the second jaw member is in a constrained state as the handle assembly is being actuated.

In some methods, the proximal actuator rod, the biasing member, and the distal actuator rod may distally move together when the second jaw member is in an unconstrained state as the handle assembly is being actuated.

In aspects, the method may further include returning the suture passer to the closed condition; and withdrawing the suture passer from the internal surgical site.

Any of the above aspects, to the extent consistent, may be utilized with any or all of the other aspects detailed herein.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Various aspects and features of the present disclosure are described hereinbelow with references to the drawings, wherein:

FIG. 3A is a first side view of the cannula of FIG. 2 with the housing removed;

FIG. 3B is a second side view rotated 90 degrees from the cannula of FIG. 3A with the housing removed;

FIG. 7 is an enlarged view of the area of detail labeled "7" in FIG. 5, illustrating the end effector assembly in a closed configuration;

FIG. 8 is a longitudinal cross-sectional view of components of the suture passer of FIG. 5, illustrating the end effector assembly in the closed configuration;

FIG. 9 is a longitudinal cross-sectional view of components of the suture passer of FIG. 5, illustrating the end effector assembly in an open configuration;

FIG. 10 is an enlarged perspective view of the end effector assembly of FIG. 5, illustrated in the open configuration.

DETAILED DESCRIPTION OF THE EMBODIMENTS

Figure 1:
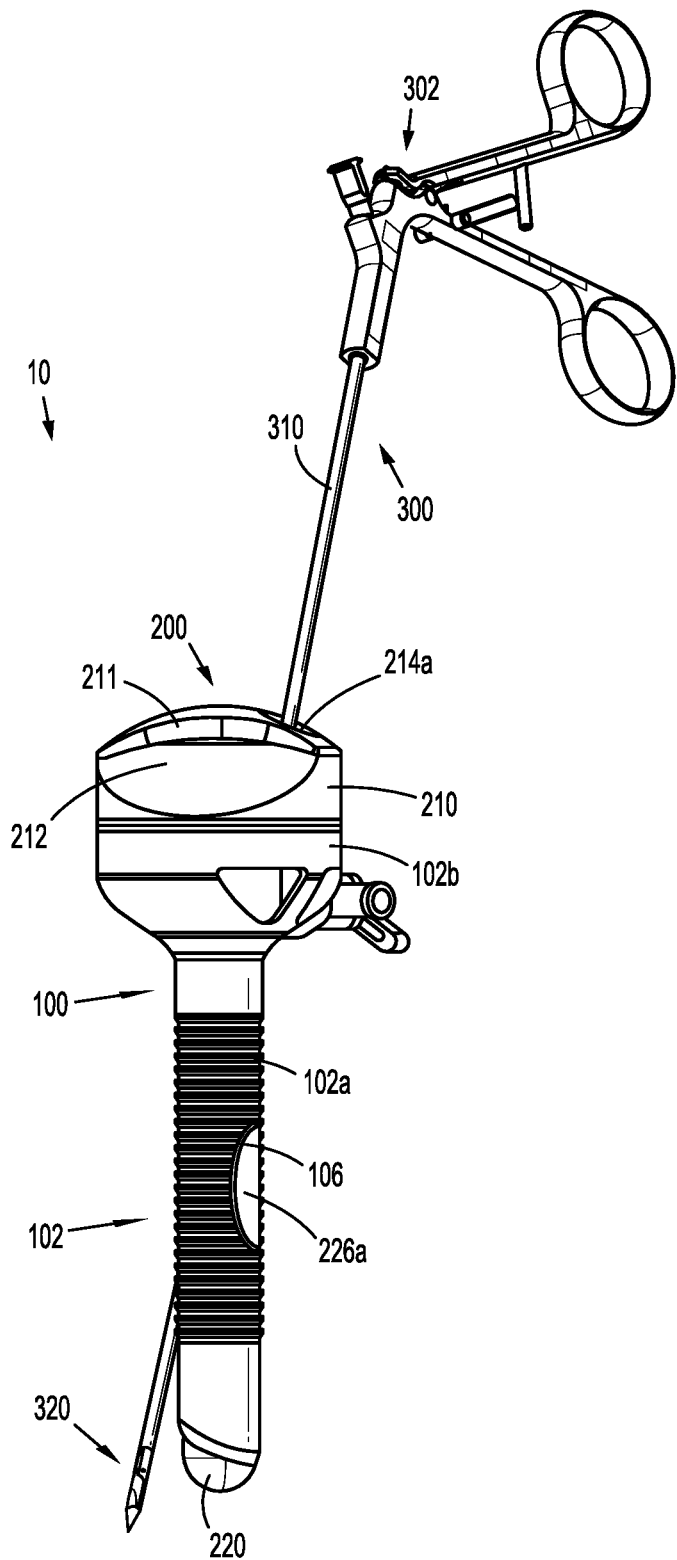
FIG. 1 is a perspective view of a wound closure system provided in accordance with the present disclosure including a cannula, a guide member, and a suture passer.

As detailed below and illustrated in the figures, the present disclosure provides devices, systems, and methods that facilitate accessing an internal surgical site through an opening in tissue, performing one or more minimally-invasive surgical tasks within the internal surgical site, and closing the opening in tissue once the surgical task(s) is complete. In the accompanying figures and in the description that follows, in which like reference numerals identify similar or identical elements, the term "proximal" will refer to the end of the device or portion thereof which is closest to the clinician during use, while the term "distal" will refer to the end or portion which is farthest from the clinician during use, as is traditional.

The present disclosure provides a suture passer having an overstroke assembly that prevents damage to an end effector assembly of the suture passer when the end effector assembly is in a constrained state. The end effector assembly of the suture passer has a first jaw member, and a second jaw member movable relative to the first jaw member between an open configuration, and a closed configuration, in which the jaw members grasp a suture therebetween. In some instances, the second jaw member of the suture passer may be prevented from opening due to an obstruction present in the surgical site (e.g., a surgical instrument, hard tissue, or the like). In these instances, when a clinician actuates a handle assembly of the suture passer in an attempt to open the second jaw member, one or more internal components of the suture passer are vulnerable to damage if the clinician continues to apply an actuating force. The overstroke assembly of the present disclosure includes a proximal actuator rod operably coupled to the handle assembly, a distal actuator rod operably coupled to the second jaw member, and a biasing member disposed between the proximal and distal actuator rods. The biasing member compresses between the proximal and distal actuator rods during an overstroke by the clinician to prevent the distal actuator rod from damaging a pivot member that couples the second jaw member with the distal actuator rod.

With reference to FIG. 1, a surgical assembly for facilitating a wound closure is shown generally identified by reference numeral 10. The surgical assembly or wound closure system 10 generally includes a cannula 100, a guide member 200, and a suture passer 300. Briefly, in use of the surgical assembly 10, a trocar (not shown) may be first utilized to create and/or expand an opening in tissue and to subsequently position the cannula 100 therein; the cannula 100 is utilized to protect surrounding tissue, maintain insufflation, and/or guide surgical instrumentation (not shown) into an internal surgical site; the guide member 200 is inserted into the cannula 100 and utilized to facilitate insertion and withdrawal of the suture passer 300 through the tissue adjacent the opening; and the suture passer 300 is utilized to deposit and/or retrieve a portion of suture to/from the internal surgical site on either side of the opening in tissue to enable tying off of the suture to close the opening.

Figure 2:
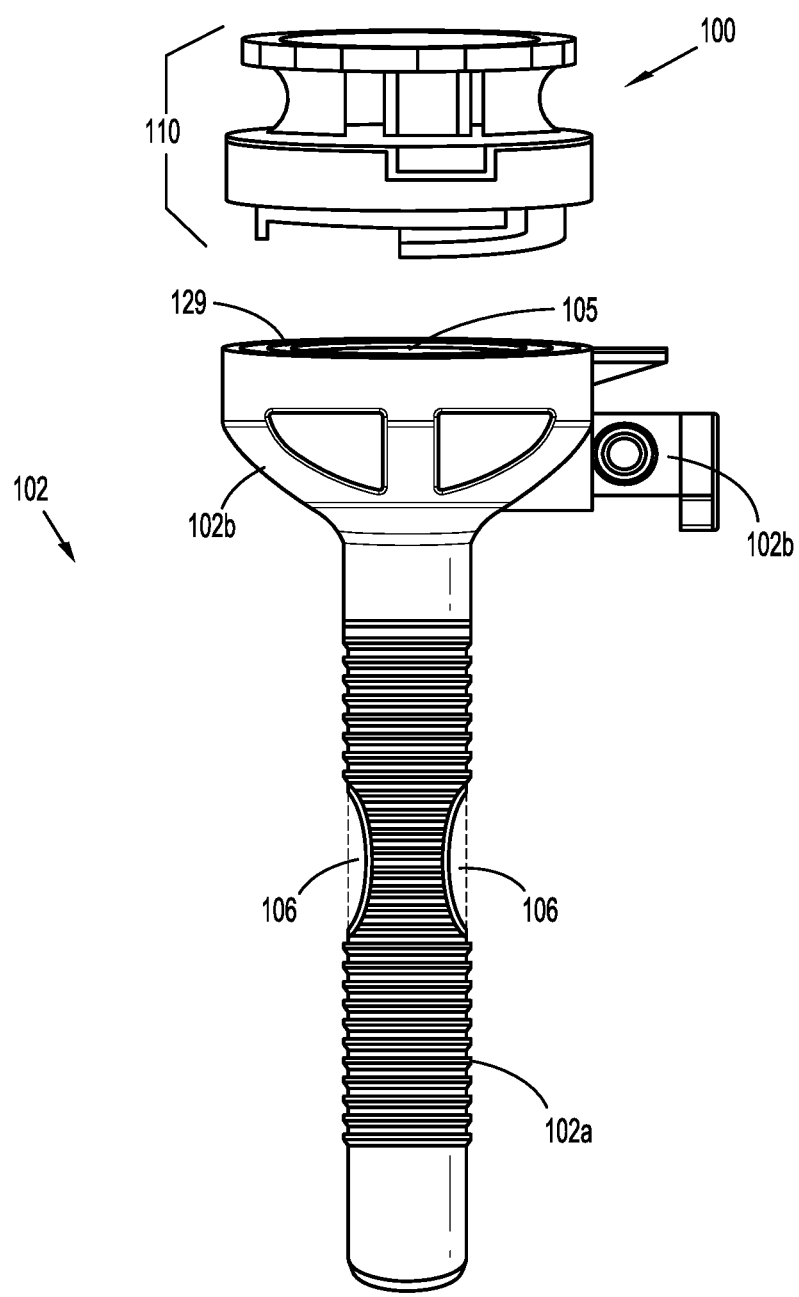
FIG. 2 is a side perspective view of the cannula of FIG. 1 with a housing and an elongated portion of the cannula shown separated from each other.

With reference to FIGS. 2, 3A, and 3B, the cannula 100 of the surgical assembly 10 (FIG. 1) includes an elongated portion 102 and a housing 110. The elongated portion 102 includes an elongated tubular member 102a and a base member 102b. The base member 102b is configured to couple the housing 110 and the elongated portion 102 to one another. The elongated tubular member 102a extends distally from the base member 102b and may be formed from a translucent material, although other materials are also contemplated. The elongated tubular member 102a of the cannula 100 may be provided in various configurations, e.g., various diameters between about 10 mm to about 15 mm and/or various lengths from about 70 mm to about 150 mm, although other suitable configurations are also contemplated. The elongated tubular member 102a is configured for positioning within an opening in tissue and defines a longitudinal passageway 105 extending therethrough that is configured to receive surgical instrumentation (not shown) for guiding the surgical instrumentation (not shown) through the opening in tissue and into the internal surgical site. The passageway 105 of the elongated tubular member 102a is configured to receive the guide member 200 (FIGS. 1 and 4) to facilitate closure of the opening in tissue after completion of the surgical procedure, as detailed below.

The elongated portion 102 of the cannula 100 has a pair of opposed slots 106 extending through an annular side wall of the elongated tubular member 102a, thus providing lateral access to and from the longitudinal passageway 105 to and from the exterior of the elongated tubular member 102a. The opposed slots 106 may be positioned along the length of the elongated tubular member 102a at any suitable position, e.g., closer to or further from the base member 102b of the elongated portion 102 of the cannula 100. For some procedures, it has been found to be desirable that, once the cannula 100 is positioned within the opening in tissue, the slots 106 are located on the elongated tubular member 102a at a position distal of the skin and fatty layers of tissue and adjacent to the fascia and muscle layers of tissue. This is desirable because the fascia and muscle layers are better suited to receive and retain a suture for closing the opening in tissue. Thus, a cannula 100 having the slots 106 positioned to achieve this function may be selected. However, other configurations are also contemplated.

For a more detailed description of embodiments of cannulas for use in the surgical assembly 10 of the present disclosure, reference may be made to U.S. Pat. No. 9,700,303, filed Jul. 29, 2014, the entire contents of which being incorporated by reference herein.

Figure 4:
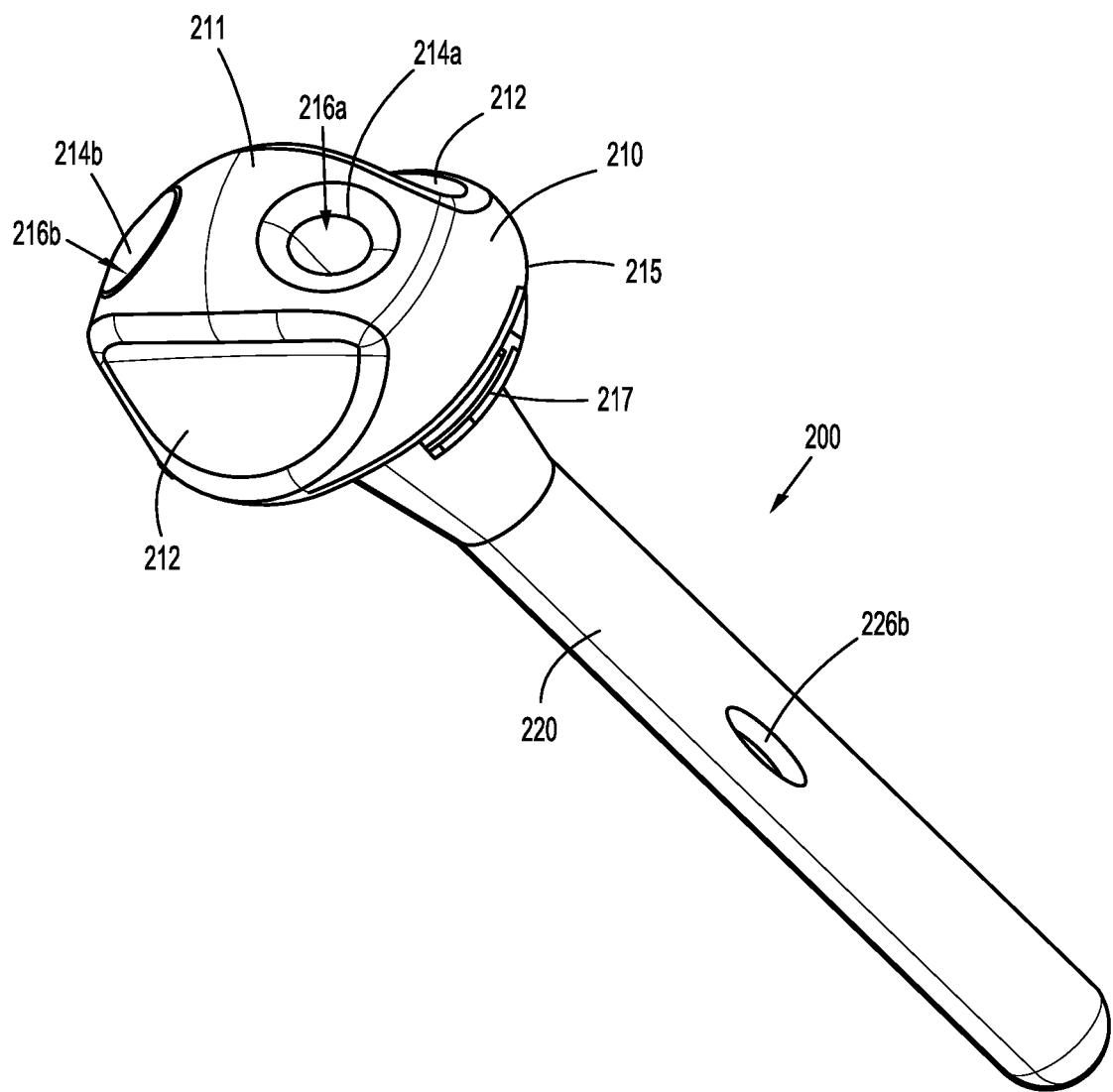
FIG. 4 is a proximal perspective view of the guide member of FIG. 1.
Figure 5:
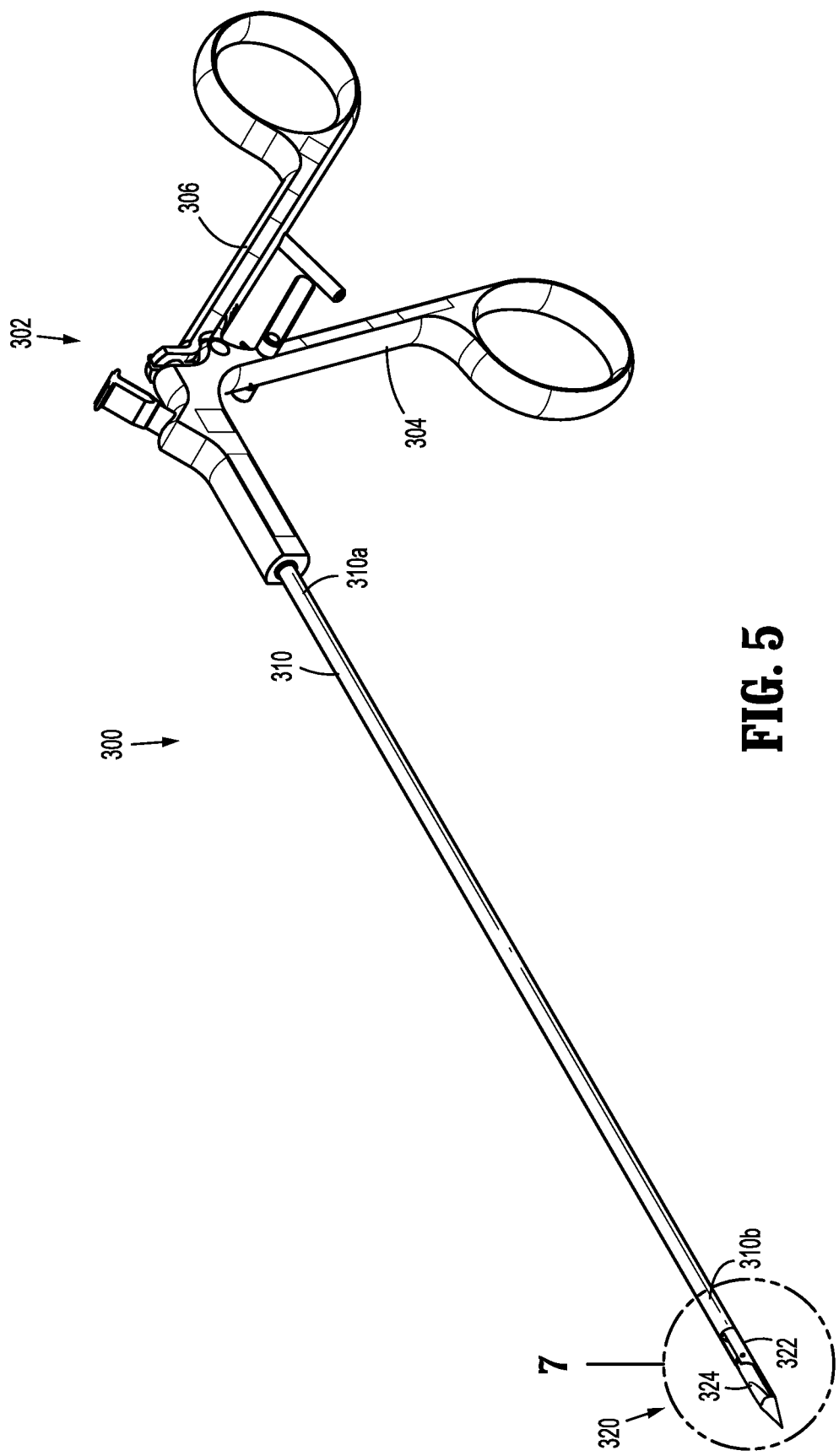
FIG. 5 is a side perspective view of the suture passer of FIG. 1.
Figure 6:
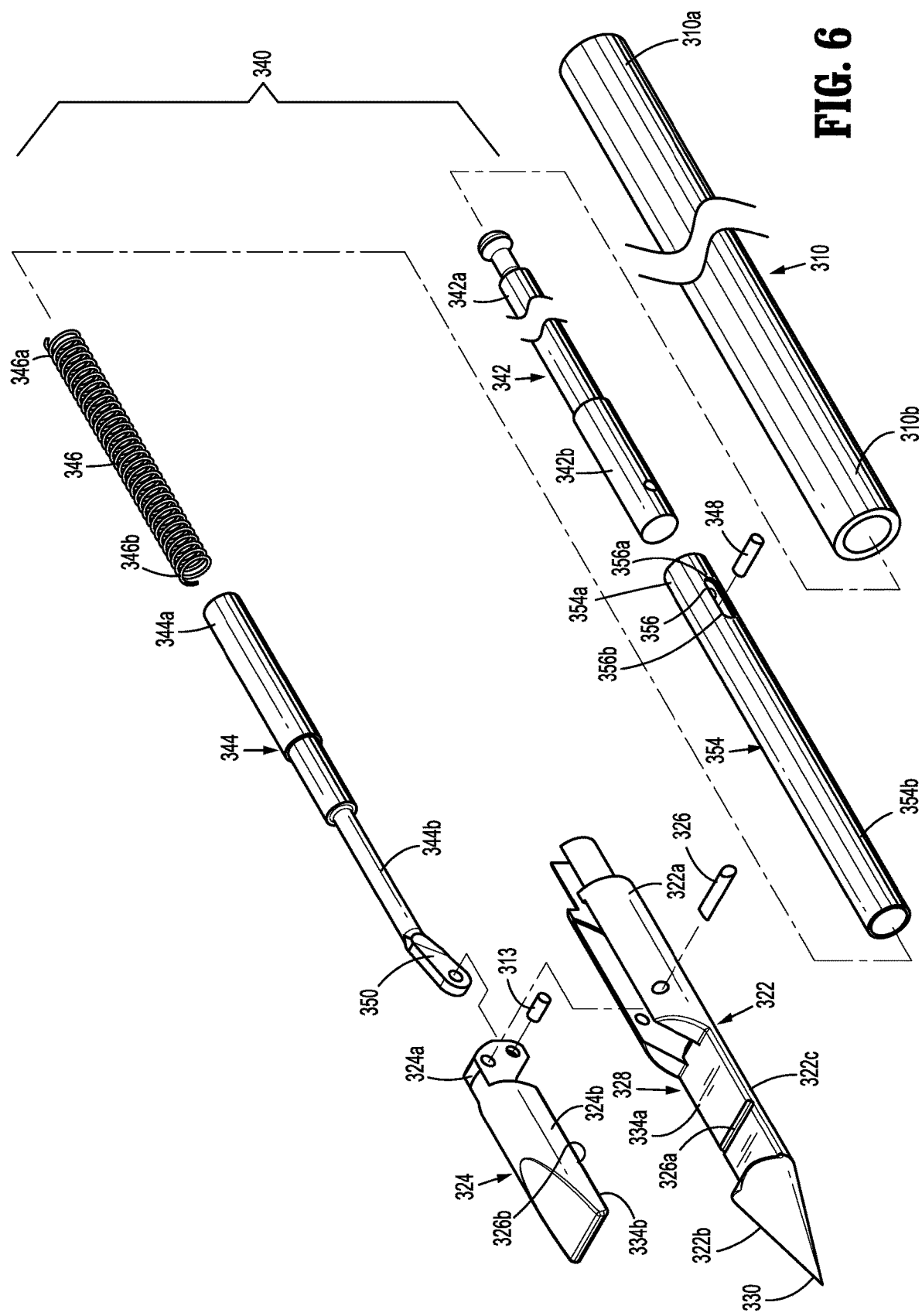
FIG. 6 is an exploded view of a shaft, an end effector assembly, and an overstroke assembly of the suture passer of FIG. 5.

With reference to FIGS. 1 and 4, the guide member 200 of the surgical assembly 10 is illustrated. The guide member 200 is configured for use with the cannula 100 to facilitate closure of an opening in tissue after completion of one or more surgical tasks. More specifically, the guide member 200 is configured for releasable engagement within the elongated portion 102 of the cannula 100 to guide passage of a suitable suture passer, e.g., suture passer 300 (see FIGS. 1 and 5-11), through an opening in tissue and into the internal surgical site to deposit and/or retrieve a portion of a suture, thus facilitating closure of the opening in the tissue.

The guide member 200 generally includes a guide housing 210 disposed in mechanical cooperation with an elongated guide shaft 220. The guide member 200 further includes a pair of guide lumens 216a, 216b extending therethrough. The guide housing 210 defines a proximally-facing portion 211 including a pair of recesses 212 that facilitate grasping and manipulation of the guide member 200 and a pair of apertures 214a, 214b that communicate with the proximal ends of respective lumens 216a, 216b extending through the guide member 200. The guide housing 210 further includes threading 217 defined on a distally-facing portion 215 thereof that is configured to engage complementary threading 129 (FIG. 2) of the base member 102b of the cannula 100, e.g., via a bayonet connection, to releasably engage and align the guide housing 210 and the elongated portion 102 of the cannula 100 relative to one another.

The elongated guide shaft 220 of the guide member 200 extends distally from the guide housing 210 and is configured for insertion through the passageway 105 (FIG. 2) of the elongated tubular member 102a of the cannula 100 after having removed the housing 110 of the cannula 100 from the base member 102b of the cannula 100. The elongated shaft 220 includes a pair of opposed slots 226a (FIG. 1), 226b (FIG. 4) defined through the annular side wall of the elongated shaft 220 that communicate with the distal ends of respective lumens 216a, 216b extending through the guide member 200. That is, the lumens 216a, 216b extend between respective apertures 214a, 214b defined through the proximally-facing portion 211 of the guide housing 210 and respective slots 226a, 226b defined through the annular side wall of the elongated shaft 220. As such, and as will be detailed below, a suture passer, e.g., suture passer 300 (FIG. 1), may then be inserted through one of the lumens 216a, 216b of the guide member 200, the corresponding slot 106 of the cannula 100, tissue, and into the internal surgical site to facilitate closure of the opening in tissue.

For a more detailed description of embodiments of a guide member for use in the surgical assembly 10 of the present disclosure, reference may be made to U.S. Pat. No. 9,700,303, filed Jul. 29, 2014, the entire contents of which having been incorporated by reference above.

With reference to FIGS. 1 and 5-11, an embodiment of a suture passer 300 configured for use with the cannula 100 and the guide member 200 is described. As detailed below, the suture passer 300 is transitionable between an insertion/withdrawal/piercing condition (FIGS. 1, 5, 7, 8, and 11), and an expanded/deployed condition (FIGS. 9 and 10) and includes an overstroke assembly 340 for effecting the transition between these conditions. The suture passer 300 generally includes a handle assembly 302, a shaft or tubular member 310 extending distally from the handle assembly 302, and an end effector assembly 320 coupled to a distal end portion 310b of the shaft 310. The handle assembly 302 has a fixed handle portion 304 and a trigger 306 pivotably coupled to the fixed handle portion 304. To actuate the end effector assembly 320, a clinician moves the trigger 306 of the handle assembly 302 in relation to the fixed handle portion 304 to approximate or space the trigger 306 and the fixed handle portion 304.

The shaft 310 of the suture passer 300 may be flexible to permit insertion through any of the lumens 216a, 216b of the guide member 200. Alternatively, the shaft 310 may have a rigid, curved configuration having a radius of curvature equal to that of the lumens 216a, 216b of the guide member 200 for use therewith, or may have a rigid, linear configuration. The shaft 310 has a proximal end portion 310a fixed to the fixed handle portion 304 of the handle assembly 302. The shaft 310 serves as a barrier to inhibit contact between the internal components of the suture passer 300 and surgical instrumentation (not shown) and/or tissue through which the suture passer 300 is inserted, thus inhibiting rubbing or catching of the internal components of the suture passer 300 upon the surgical instrumentation (not shown) and/or tissue during actuation of the suture passer 300.

The end effector assembly 320 of the suture passer 300 has a first jaw member 322 fixed to the distal end portion 310b of the shaft 310, and a second jaw member 324 coupled to the first jaw member 322 and configured to pivot relative to the first jaw member 322 between a closed configuration, as shown in FIG. 7, and an open configuration, as shown in FIG. 10. With specific reference to FIG. 6, the first jaw member 322 has a proximal end portion 322a, an intermediate portion 322c, and a distal end portion 322b. Similarly, the second jaw member 324 has a proximal end portion 324a and a distal end portion 324b. The intermediate portion 322c of the first jaw member 322 defines a recessed portion 328 dimensioned for receipt of the distal end portion 324b of the second jaw member 324 upon the second jaw member 324 entering the closed configuration. In the closed configuration, the distal end portion 324b of the second jaw member 324 is nested with the recessed portion 328 of the second jaw member 324, such that each of the first and second jaw members 322, 324 cooperatively assume a tubular configuration that is streamlined with the shaft 310 to facilitate passage of the end effector assembly 320 through the guide member 200 (FIG. 4) and the cannula 100 (FIG. 2). The distal end portion 322b of the first jaw member 322 may have a sharpened or pointed distal piercing tip 330 configured to facilitate piercing through tissue.

The proximal end portion 322a of the first jaw member 322 and the proximal end portion 324a of the second jaw member 324 have a pivot pin 326 extending transversely therethrough to pivotably couple the second jaw member 324 to the first jaw member 322. In alternate embodiments, rather than being pivotably coupled to the first jaw member 322, the second jaw member 324 may be directly pivotably coupled to the distal end portion 310b of the shaft 310. The proximal end portion 324a of the second jaw member 324 may be set at an obtuse angle from the remainder of the second jaw member 324.

The first and second jaw members 322, 324 each have a planar suture-contacting surface 334a, 334b opposing one another when the first and second jaw members 322, 324 are in the closed configuration. Each of the suture-contacting surfaces 334a, 334b defines a notch 336a, 336b therein that extends across the respective first and second jaw members 322, 324. The notches 336a, 336b of the first and second jaw members 322, 324 are configured to cooperatively define a channel 338 (FIG. 8) to enclose a suture upon the first and second jaw members 322, 324 assuming the closed configuration, as shown in FIG. 11.

Figure 11:
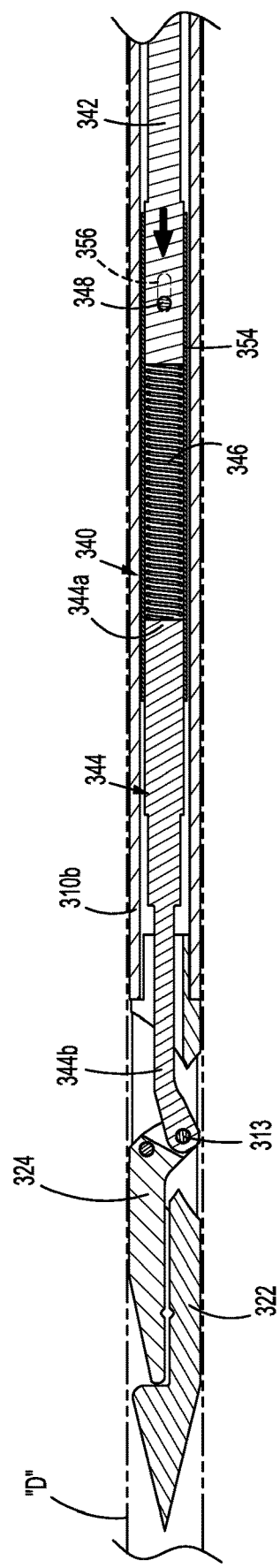
FIG. 11 is a longitudinal cross-sectional view of components of the suture passer of FIG. 5, illustrating the overstroke assembly after having been triggered.

With reference to FIGS. 6-11, the suture passer 300 includes an overstroke assembly 340 movably received in the shaft 310 and configured to effect an actuation of the end effector assembly 320 while protecting components of the suture passer 300 (e.g., the actuation pin 313) from being damaged. In particular, the overstroke assembly 340 prevents damage to the suture passer 300 when the end effector assembly 320 is in a constrained state, i.e., when the second jaw member 324 is prevented from opening due to an obstruction "O" in a body cavity or in tissue (FIG. 11). The overstroke assembly 340 includes a proximal actuator rod 342, a distal actuator rod 344, and a biasing member 346 interposed between the proximal and distal actuator rods 342, 344. The proximal actuator rod 342 is disposed within the shaft 310 and is longitudinally movable therein. The proximal actuator rod 342 has a proximal end portion 342a operably coupled to the trigger 306 of the handle assembly 302 (FIG. 5), such that a first actuation of the handle assembly 302 (e.g., an approximation of the trigger 306 and the fixed handle portion 304) retracts the proximal actuator rod 342 within the shaft 310, and a second actuation of the handle assembly 302 (e.g., a spacing of the trigger 306 from the fixed handle portion 304) advances the proximal actuator rod 342 within the shaft 310. The proximal actuator rod 342 has a distal end portion 342b disposed within the distal end portion 310b of the shaft 310 and abuts a proximal end portion 346a of the biasing member 346. The distal end portion 342b of the proximal actuator rod 342 has a transversely-extending pin 348 axially fixed thereto, as will be described. In embodiments, the biasing member 346 may be a coil spring, with other types of biasing members being contemplated.

The distal actuator rod 344 of the overstroke assembly 340 is disposed within the distal end portion 310b of the shaft 310 and is longitudinally movable therein. The distal actuator rod 344 has a proximal end portion 344a in abutting engagement with a distal end portion 346b of the biasing member 346, and a distal end portion 344b. The distal end portion 344b of the distal actuator rod 344 has a connector 350 set at an obtuse angle from the remainder of the distal actuator rod 344. The connector 350 rotationally couples the proximal end portion 324a of the second jaw member 324 to the distal actuator rod 344 via the actuation pin 313. As will be described, under normal operating conditions, distal movement of the distal actuator rod 344 transitions the second jaw member 324 toward the open configuration using the actuation pin 313 of the second jaw member 324.

The overstroke assembly 340 may further include an outer sleeve 354 disposed within the shaft 310 and longitudinally movable therein. The sleeve 354 houses the biasing member 346 and has a proximal end portion 354a disposed about the distal end portion 342b of the proximal actuator rod 342, and a distal end portion 354b disposed about the proximal end portion 344a of the distal actuator rod 344. The proximal actuator rod 342 is slip fit within the sleeve 354, such that the proximal actuator rod 342 is movable relative to the sleeve 354, whereas the distal actuator rod 344 is press-fit within the sleeve 354, such that the sleeve 354 and the distal actuator rod 344 translate within the shaft 310 together during actuation of the suture passer 300.

The sleeve 354 defines a pair of opposed longitudinally-extending slots 356 in the proximal end portion 354a thereof. The pin 348 of the proximal actuator rod 342 extends through the slots 356 of the sleeve 354 to permit translation of the proximal actuator rod 342 relative to the sleeve 354 between a proximal position, in which the pin 348 is engaged with a proximal limit 356a of the slots 356, and a distal position, in which the pin 348 is engaged with a distal limit 356b of the slots 356. With the pin 348 disposed in the proximal position, a retraction of the proximal actuator rod 342 results in a retraction of the sleeve 354, and, in turn, the distal actuator rod 344 and the biasing member 346, to close the second jaw member 324. With the pin 348 disposed in the proximal position and when the second jaw member 324 is in the constrained state, advancement of the proximal actuator rod 342 translates the pin 348 from the proximal position toward the distal position within the slots 356 of the sleeve 354, thereby compressing the biasing member 346 between the proximal actuator rod 342 and the distal actuator rod 344. In contrast, with the pin 348 disposed in the proximal position and when the second jaw member 324 is in an unconstrained state, advancement of the proximal actuator rod 342 urges the biasing member 346 with a sufficient amount of force (without compressing the biasing member 346) to advance the biasing member 346, the distal actuator rod 344, and the sleeve 354 as an integral unit, thereby opening the second jaw member 324.

In operation, as shown in FIG. 9, the second jaw member 324 of the suture passer 300 is disposed in the open configuration with the pin 348 of the proximal actuator rod 342 disposed in the proximal position relative to the slots 356 of the sleeve 354. As such, a portion of suture may be positioned within or removed from the notches 336a, 336b of the first and second jaw members 322, 324. In order to prepare the suture passer 300 for insertion into the surgical site, the suture passer 300 is transitioned to the insertion/withdrawal condition (FIG. 8) by depressing or translating the trigger 306 distally relative to the fixed handle portion 304. Depressing the trigger 306 relative to the fixed handle portion 304 translates the proximal actuator rod 342 proximally relative to the shaft 310, thereby pulling the sleeve 354, the distal actuator rod 344, and the biasing member 346 proximally therewith as an integral unit. Since the actuation pin 313 of the distal actuator rod 344 is coupled to the second jaw member 324 at an offset location relative to the pivot pin 326, proximal translation of the actuation pin 313 of the distal actuator rod 344 rotates the second jaw member 324 toward the closed configuration, as shown in FIG. 8.

With the second jaw member 324 in the closed configuration (FIGS. 1, 5, 7, 8, and 11), the suture passer 300 may be inserted through one of the lumens 226a, 226b of the guide member 200 (FIG. 4) and into contact with tissue surrounding an opening in the tissue. Upon contacting tissue, the distal piercing tip 330 of the first jaw member 322 advances the tissue passer 300 through the tissue until reaching the internal surgical site. Once the suture passer 300 has been inserted through the guide member 200, tissue, and into the internal surgical site, the suture passer 300 may be returned to the open configuration (FIGS. 9 and 10) by pulling or retracting the trigger 306 proximally away from the fixed handle portion 304. Pulling the trigger 306 proximally away from the fixed handle portion 304 advances the proximal actuator rod 342 relative to the shaft 310 and urges the biasing member 346 distally. Distal translation of the biasing member 346 effects a distal translation of the distal actuator rod 344 and the sleeve 354, whereby the actuation pin 313 cams open the second jaw member 324. In the open configuration, as shown in FIG. 9, a portion of suture may be positioned within or removed from the notches 336a, 336b in the first and second jaw members 322, 324. Ultimately, the suture passer 300 may be returned to the closed configuration (FIGS. 1, 5, 7, 8, and 11) as detailed above, and withdrawn from the internal surgical site. As the suture passer is withdrawn from the surgical site through tissue, the suture is pulled through the tissue to close the opening in the tissue.

In some instances, an attempt to transition the end effector assembly 320 to the open configuration via the second actuation of the handle assembly 302 fails due to the second jaw member 324 being constrained from opening due to an obstruction "O" (FIG. 11) in the surgical site. Under such circumstances, given that the constrained jaw member 324 prevents the distal actuator rod 344 from moving distally, a distally-oriented force applied on the biasing member 346 via the proximal actuator rod 342 overcomes the spring force of the biasing member 346 to compress the biasing member 346 between the proximal and distal actuator rods 342, 344. As such, the pin 348 of the proximal actuator rod 342 is free to move distally relative to the sleeve 354 from the proximal position within the slots 356 of the sleeve 354 to the distal position within the slots 356 of the sleeve 354 throughout the entire second actuation of the handle assembly 302. In this way, the biasing member 346, rather than the actuation pin 313, absorbs the distally-oriented force originating from the clinician's second actuation of the handle assembly 302 to prevent damage to the actuation pin 313 and also to tissue at the surgical site. In the absence of the overstroke assembly 340, the entire distally-oriented force of the proximal actuator rod 342 would ultimately be absorbed by the actuation pin 313, which would likely shear under such force and prevent reuse of the suture passer 300.

The suture passer 300 may be configured for selective disassembly (and be made of sterilizable reusable and/or disposable components) to facilitate cleaning and/or replacement of disposable components.

Any suitable suture or sutures may be utilized in conjunction with the above. In particular, the suture(s) may be provided in any suitable form and/or include any suitable feature(s) to facilitate insertion through and depositing the suture within the internal surgical site on one side of the opening in tissue, and retrieval and withdrawal of the portion of suture from the other side of the opening in tissue. Such a configuration establishes a "U"-shaped suture extending through tissue on either side of the opening and across the opening on the internal side of tissue. This configuration enables tying off of the externally-disposed free ends of the suture and provides sufficient holding strength to permit healing and resist re-opening of the sutured tissue.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A suture passer, comprising:
   a shaft;
   a first jaw member coupled to a distal end portion of the shaft;
   a second jaw member pivotable relative to the first jaw member between open and closed configurations; and
   an overstroke assembly including:
      a proximal actuator rod;
      a distal actuator rod axially movable relative to the shaft and operably coupled to the second jaw member; and
      a spring interposed between the proximal and distal actuator rods, wherein distal movement of the proximal actuator rod distally moves the spring and the distal actuator rod to pivot the second jaw member relative to the first jaw member to the open configuration, the spring being configured to compress to allow for independent distal movement of the proximal actuator rod relative to the distal actuator rod in response to an obstruction of the second jaw member.

2. The suture passer according to claim 1, wherein the overstroke assembly further includes a sleeve disposed within the shaft and longitudinally movable relative to the shaft, the sleeve being disposed about the proximal and distal actuator rods and housing the spring.

3. The suture passer according to claim 2, wherein the sleeve defines a longitudinally-extending slot, the proximal actuator rod having a pin slidably received in the slot.

4. The suture passer according to claim 3, wherein when the second jaw member is prevented from opening by an obstruction, an actuation of a handle assembly distally moves the pin from a proximal position within the slot to a distal position within the slot.

5. The suture passer according to claim 4, wherein the proximal actuator rod is configured to move relative to the sleeve and the distal actuator rod during the distal movement of the pin toward the distal position.

6. The suture passer according to claim 3, wherein the pin is configured to proximally move the sleeve and the distal actuator rod to move the second jaw member toward the closed configuration.

7. The suture passer according to claim 2, wherein the distal actuator rod is fixed within the sleeve, and the proximal actuator rod is slip-fit within the sleeve.

8. The suture passer according to claim 1, wherein the second jaw member has a proximal end portion pivotably coupled to the distal actuator rod.

9. The suture passer according to claim 1, wherein the first jaw member has a distal tip configured to pierce tissue.

10. The suture passer according to claim 1, wherein the second jaw member is nested with the first jaw member in the closed configuration.

11. The suture passer according to claim 10, wherein the first jaw member defines a recessed portion configured to receive the second jaw member when the second jaw member is in the closed configuration.

12. The suture passer according to claim 1, wherein each of the first and second jaw members has a suture-contacting surface defining a transverse notch therein, wherein the transverse notches of the first and second jaw members are configured to cooperatively enclose a suture therein.

13. A suture passer, comprising:
    a handle assembly;
    a shaft extending distally from the handle assembly;
    an end effector assembly including:
       a first jaw member coupled to a distal end portion of the shaft; and
       a second jaw member pivotable relative to the first jaw member between open and closed configurations;
    a proximal actuator rod operably coupled to a trigger of the handle assembly, such that a first actuation of the trigger proximally moves the proximal actuator rod;
    a distal actuator rod slidably disposed within the shaft and operably coupled to the second jaw member;
    a spring interposed between the proximal and distal actuator rods, wherein the proximal actuator rod is configured to distally move the distal actuator rod via the spring in response to a second actuation of the handle assembly, and wherein the spring is configured to compress between the proximal and distal actuator rods upon the proximal actuator rod exerting a distally-oriented, threshold force on the spring; and
    a sleeve disposed within the shaft and longitudinally movable relative to the shaft, the sleeve being disposed about the proximal and distal actuator rods and housing the spring.

14. The suture passer according to claim 13, wherein the distal actuator rod is pivotably coupled to the second jaw member via a pivot pin configured to receive a distally-oriented force from the distal actuator rod, the distally-oriented, threshold force imparted on the spring being lower than a threshold force required to damage the pivot pin.

15. The suture passer according to claim 13, wherein when the second jaw member is prevented from opening by an obstruction, the second actuation of the trigger distally moves the proximal actuator rod relative to the distal actuator rod to compress the spring therebetween.

16. The suture passer according to claim 13, wherein the sleeve defines a longitudinally-extending slot, the proximal actuator rod having a pin slidably received in the slot.

17. The suture passer according to claim 16, wherein when the second jaw member is prevented from opening by an obstruction, the second actuation of the trigger distally moves the pin from a proximal position within the slot to a distal position within the slot.

18. The suture passer according to claim 17, wherein the proximal actuator rod is configured to move relative to the sleeve and the distal actuator rod during the distal movement of the pin toward the distal position.

19. The suture passer according to claim 18, wherein the pin is configured to proximally move the sleeve and the distal actuator rod to move the second jaw member toward the closed configuration in response to the first actuation of the trigger.

20. The suture passer according to claim 17, wherein the distal actuator rod is fixed within the sleeve, and the proximal actuator rod is slip-fit within the sleeve.

21. A method of depositing a portion of a suture into an internal surgical site and/or retrieving a portion of suture from within an internal surgical site, comprising: advancing a suture passer into a surgical site while first and second jaw members of the suture passer are in a closed configuration; and actuating a handle assembly of the suture passer to distally move a proximal actuator rod, proximal and distal ends of a spring, and a distal actuator rod together, whereby the distal actuator rod pivots the second jaw member relative to the first jaw member to transition the first and second jaw members to the open configuration for one of depositing a portion of suture into the internal surgical site or retrieving a portion of the suture from the internal surgical site.

22. The method according to claim 21, wherein the spring is compressed between the proximal and distal actuator rods when the second jaw member is in a constrained state as the handle assembly is being actuated.

23. The method according to claim 22, wherein the proximal actuator rod, the spring, and the distal actuator rod distally move together when the second jaw member is in an unconstrained state as the handle assembly is being actuated.

24. The method according to claim 21, further comprising:
- returning the suture passer to the closed condition; and
- withdrawing the suture passer from the internal surgical site.

* * * * *